(12) United States Patent
Bimek

(10) Patent No.: US 10,034,794 B2
(45) Date of Patent: Jul. 31, 2018

(54) DEVICE FOR CONTRACEPTION FOR USE BY A MAN

(71) Applicant: PES Innovation AG, Herisau (CH)

(72) Inventor: Clemens Bimek, Schafisheim (CH)

(73) Assignee: PES INNOVATION AG, Herisau (CH)

( * ) Notice: Subject to any disclaimer, the term of this patent is extended or adjusted under 35 U.S.C. 154(b) by 87 days.

(21) Appl. No.: 15/302,471

(22) PCT Filed: Mar. 26, 2015

(86) PCT No.: PCT/IB2015/052224
§ 371 (c)(1),
(2) Date: Oct. 6, 2016

(87) PCT Pub. No.: WO2015/155618
PCT Pub. Date: Oct. 15, 2015

(65) Prior Publication Data
US 2017/0020719 A1    Jan. 26, 2017

(30) Foreign Application Priority Data

Apr. 8, 2014 (CH) ...................................... 0542/14

(51) Int. Cl.
*A61F 6/24* (2006.01)
*A61F 6/20* (2006.01)

(52) U.S. Cl.
CPC . *A61F 6/24* (2013.01); *A61F 6/20* (2013.01)

(58) Field of Classification Search
CPC ...... A61F 6/24; A61F 6/20; A61F 6/22; A61F 5/41; A61F 2006/042; A61F 6/02;

(Continued)

(56) References Cited

U.S. PATENT DOCUMENTS

| 4,200,107 A | 4/1980 | Reid |
| 6,513,528 B2 | 2/2003 | Burton et al. |
| 8,616,212 B1 | 12/2013 | Logan |

FOREIGN PATENT DOCUMENTS

| DE | 199 09 427 C1 | 5/2000 |
| WO | 2010/047644 A1 | 4/2010 |

OTHER PUBLICATIONS

International Preliminary Report on Patentability and Written Opinion of the International Searching Authority (English translation); for international application No. PCT/IB2015/052224; dated Oct. 12, 2016; 10 pages.

(Continued)

*Primary Examiner* — Ophelia A Hawthorne
(74) *Attorney, Agent, or Firm* — Seed IP Law Group LLP

(57) ABSTRACT

The disclosure relates to a vas deferens valve for contraception for use in a man and for implanting in the vas deferens within the scrotum, enabling the regulating of sperm flow in the vas deferens. There is a manually activated rocker switch which can be activated through the skin of the scrotum and which has a through-channel which, in the opened state, leads from a valve connection piece on the testicular vas deferens to a valve connection piece on the abdominal end of the vas deferens and, in the closed valve state, can be blocked on the end of the through-flow channel which faces the abdominal vas deferens end. The valve additionally has at least one outlet channel which, in the closed state of the valve, leads from the valve connection piece on the testicular end of the vas deferens out of the valve to the outside in the body of the man.

17 Claims, 4 Drawing Sheets

(58) Field of Classification Search
CPC ... A61F 6/065; A61F 6/04; F16K 5/06; A61B 17/11
See application file for complete search history.

(56) References Cited

OTHER PUBLICATIONS

European Patent Office; International Search Report for international application No. PCT/IB2015/052224; dated Jun. 30, 2015; 2 pages.
European Intention to Grant, dated Nov. 22, 2017, for European Application No. 15 721 317.4-1664, 15 pages. (with English Machine Translation).

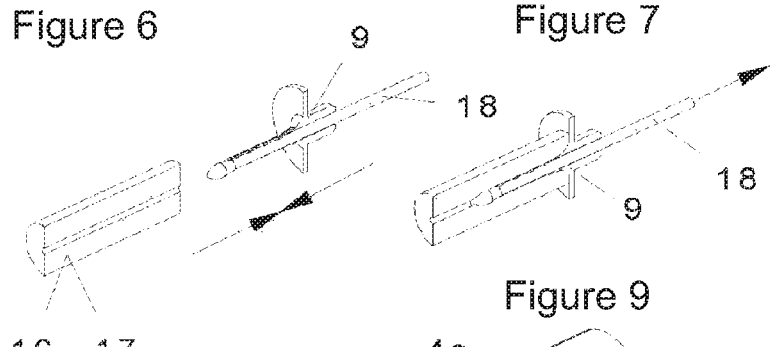

DEVICE FOR CONTRACEPTION FOR USE BY A MAN

BACKGROUND

Technical Field

The present disclosure relates to a device for contraception in a man, in particular to a device for temporarily interrupting the sperm flow within the sperm ducts (ductus deferens or vas deferens) of a man.

Description of the Related Art

The options available to a man for birth control are the known condom, which still presents an element of risk, and the almost conclusive, but reliable, vasectomy. Vasectomy reversal is associated with a great deal of effort and is not always possible. This option is therefore usually chosen only after a man has had his desired number of children.

Recently, the number of men who have undergone a vasectomy years ago and now wish to have the vasectomy reversed due to a change in living situation has increased. According to press releases by various pharmaceutical companies, the development of hormonally active medicaments intended to influence the fertility of a man has been discontinued due to a lack of success.

Devices for temporarily interrupting the sperm flow are implanted in the sperm ducts in the man's scrotum.

U.S. Pat. No. 4,200,107 describes a cylindrical vascular connector which is fitted around the sperm ducts. U.S. Pat. No. 6,513,528 describes a silicone cylinder that is to be introduced into the sperm ducts. To subsequently reverse the sperm duct blockage, in both cases a further operation is required.

Patent application PCT WO 2010/047644 A1 describes a very complicated technical solution, in which the sperm-carrying ducts are blocked by a sleeve that has to be implanted, which sleeve constricts the ducts and is operated by means of a pump device that also has to be implanted. Said pump device is supplied with energy and controlled from outside through the skin of the user. To this end, a remote control and an inductive energy transmitter are also necessary. The implantation is associated with a great deal of effort since, inter alia, at least a spinal anesthesia is necessary to eliminate pain. This leads to high surgery costs and to an increased health risk for the patient. The large number of different mechanical, hydraulic and electronic components required for said device moreover increases the risk of technical failure, and further energy costs are incurred for operation of the device.

The patent DE 19909427 C1 describes a valve which is implanted in the sperm ducts of a man and can be felt through the user's scrotum and thus opened or closed by way of a switch lever. These valves are constructed in such a way that it is possible for the user himself to influence from outside his ability to conceive, without further surgical interventions.

BRIEF SUMMARY

Embodiments of the present invention provide a device for blocking the sperm duct of a man for the purpose of contraception, which device is improved in comparison to such devices from the prior art, particularly with regard to the valve switching.

The device according to embodiments of the invention will be referred to below as a sperm duct valve.

Disclosed is an implantable sperm duct valve for contraception in a man or male animal, for controlling the sperm flow in the sperm duct ("ductus deferens" or "vas deferens" in Latin) within the scrotum. It comprises a valve and two valve connection pieces which can respectively be attached to the testicular end and abdominal end of a sperm duct that has been severed beforehand, wherein the testicular sperm duct end is the end coming from the testicle ("testis" in Latin) and the abdominal end leads to the abdomen. The valve has a manual switch, by which on the one hand the switching state of the valve can be ascertained from outside by feeling or palpation and on the other hand a change between an open and closed state can be effected.

According to aspects of the invention, the sperm duct valve has a through-channel and at least one run-off channel, wherein the through-channel in the open state of the valve leads from the valve connection piece on the testicular sperm duct to the valve connection piece at the abdominal end of the sperm duct. In the closed valve state, the end of the through-channel facing towards the abdominal sperm duct end is closed. In this closed state of the valve, a run-off channel leads from the valve connection piece at the testicular end of the sperm duct out of the valve and into the body of the man.

In one embodiment of the invention, the switch of the sperm duct valve is configured as a rocker switch.

In another embodiment of the invention, the sperm duct valve has a release pin which first has to be actuated in order to open the valve.

Embodiments of the present invention have the advantage that, in the closed state of the valve, only the abdominal sperm duct end is closed, while the testicular sperm duct end is open and the sperm can continue to be transported unhindered from this end. In addition, the run-off channel or the plurality of run-off channels allows the discharging of sperm coming from the testicular sperm duct end, which sperm can thus flow out of the valve and the housing thereof and can pass into the body of the man. Therefore, by virtue of the valve according to embodiments of the invention, no build-up of the exiting sperm occurs in the region of the epididymis. Instead, sperm pass into the tissue in the scrotum and are broken down there by the body's own mechanisms. Current knowledge suggests that this has no pathological effects.

Since the risk of sperm build-up is now omitted, the sperm duct valve according to embodiments of the invention can be implanted in the sperm duct at any location in the region of the scrotum. It is no longer absolutely necessary for the implant to be placed so close to the epididymis. This has the advantage that the implant can be implanted by the surgeon at a location best suited to the patient.

Embodiments of the present invention provide a passive implant within the sperm duct (ductus deferens) in the scrotum of a man.

The implantation of the valve requires only a simple, low-risk, inexpensive, out-patient operation under local anesthesia, similar to a vasectomy, and can be performed by any trained urologist. As in the case of a vasectomy, the sperm ducts are severed and the resulting two ends of the sperm duct are pushed onto the connection pieces of the valve which are provided for this purpose, and are fixed thereto. The sperm duct valve is able to move freely along with the sperm duct attached thereto and the testes in the scrotum. The valve is generally used in pairs, since usually there are also two testes.

The valve is constructed in such a way that the switching state of the valve, that is to say open or closed, can be ascertained by the user himself, without further surgical intervention, by feeling (palpation) from outside, through the soft skin of the scrotum, and can if necessary be changed by actuating the rocker switch. When actuated, the mechanism in each case latches in a precise, secure and perceptible manner into a respective end position: open or closed. For example, the surfaces of the rocker switch are flush with the surface of the valve body in the respective open and closed valve positions.

The valve is directional. In other words, during the implantation, care must be taken to ensure that the abdominal end of the sperm duct valve is also attached to the abdominal end of the sperm duct and, in the same sense, the testicular end of the sperm duct valve is connected to the testicular end of the sperm duct.

To this end, as is customary in all technical valves, a marking of the flow direction is applied by means of an arrow. The applied arrow thus always points in the natural rising flow direction of the sperm towards the abdomen of the person in question.

It is possible to ascertain, by feeling, whether the valve is open or closed.

The valve is open when the surface of the rocker switch located on the abdominal side of the valve is flush with the valve body and the testis-side or testicular edge of the rocker switch protrudes from the valve body.

The valve is closed when the testis-side or testicular surface of the rocker switch is flush with the valve body and the abdominal edge of the rocker switch protrudes from the valve body.

In order to close the valve, the rocker switch protruding on the side of the valve pointing towards the testis is pushed towards the testis with a rolling movement. As a result, the edge of the rocker switch pointing towards the body or towards the abdomen becomes raised and the valve position is fixedly set in a latching manner.

In order to open the valve, the release pin at the lower corner of the valve pointing towards the testis is pressed and the rocker switch is pushed with a rolling movement towards the sperm duct leading to the body. As a result, the rocker switch becomes raised on the testicular side of the valve leading to the testis.

As in the case of a vasectomy, even in the closed state the man has an almost complete ejaculation since only the amount coming from the testes, around 3-5% by volume, is missing. The feeling and switching of the valve proceeds best when the scrotum is in a soft, stretched state. The scrotum serves the purpose of controlling the temperature for the testes. For optimal sperm iogenesis, the latter require a temperature of around 3° C. below the person's body temperature. If the ambient temperature is cold, the scrotum contracts in order to warm the testes. In warm to hot conditions, it becomes soft and stretches and increases its surface area in order to cool the testes. Prior to any desired switching of the sperm duct valve, therefore, the user should warm the testes region.

The selected switch position should logically be the same for both valves.

The sperm duct valve is not perceptible in the scrotum from outside since the sperm ducts always extend from the rear side of the testis.

Embodiments of the present invention provide a simple and reliable means by which a man can himself determine, at any point in time, whether he would like to become a father in a given living situation. In a heterosexual partnership, he alone is able to and can decide whether, when and after which time interval he would like to father a child. This is made possible for him by virtue of embodiments of the invention, since he simply flips the switch. He does not have to take any medicaments or hormones and there are no ongoing costs for him. His partner does not have to risk her health by using existing contraceptives. The man need never abstain from sex and/or use any paraphernalia or keep a supply of such paraphernalia. Embodiments of the invention disclosed herein provide a novel medical product for male contraception and therefore should or can be correctly called a "contra-generative". This term does not yet exist in the nomenclature. Even this alone shows that in specialist circles it is assumed that birth control is a matter for women. This is because there are numerous options for contraception for a woman. However, the use of these means is still associated with risks and side-effects. Embodiments of the invention described herein is thus an alternative to the types of birth control known to date. It enables the man to have sole responsibility for birth control. It can be used universally due to the simplicity, the high degree of reliability, the extremely minimal side-effects and risks, and the low costs.

Exemplary embodiments and the advantages thereof will be explained in more detail in the following description, with reference to the figures.

BRIEF DESCRIPTION OF THE SEVERAL VIEWS OF THE DRAWINGS

FIG. 6 shows a valve connection piece of the sperm duct valve for insertion into a sperm duct.

FIG. 7 shows the valve connection piece inserted in a sperm duct.

FIG. 8 shows the sperm duct with a widened valve connection piece.

FIG. 9 shows two valve cap halves (4) and the integration thereof with the sperm duct valve connection piece of FIGS. 6-8.

FIG. 10 shows the assembly of the combination of sperm duct valve connection piece and valve cap halves, produced in FIG. 9, with the sperm duct valve of FIGS. 2 and 3.

In the figures, identical references have been used in each case for identical elements, and first-instance explanations relate to all figures unless mentioned otherwise.

DETAILED DESCRIPTION

Figure 1:
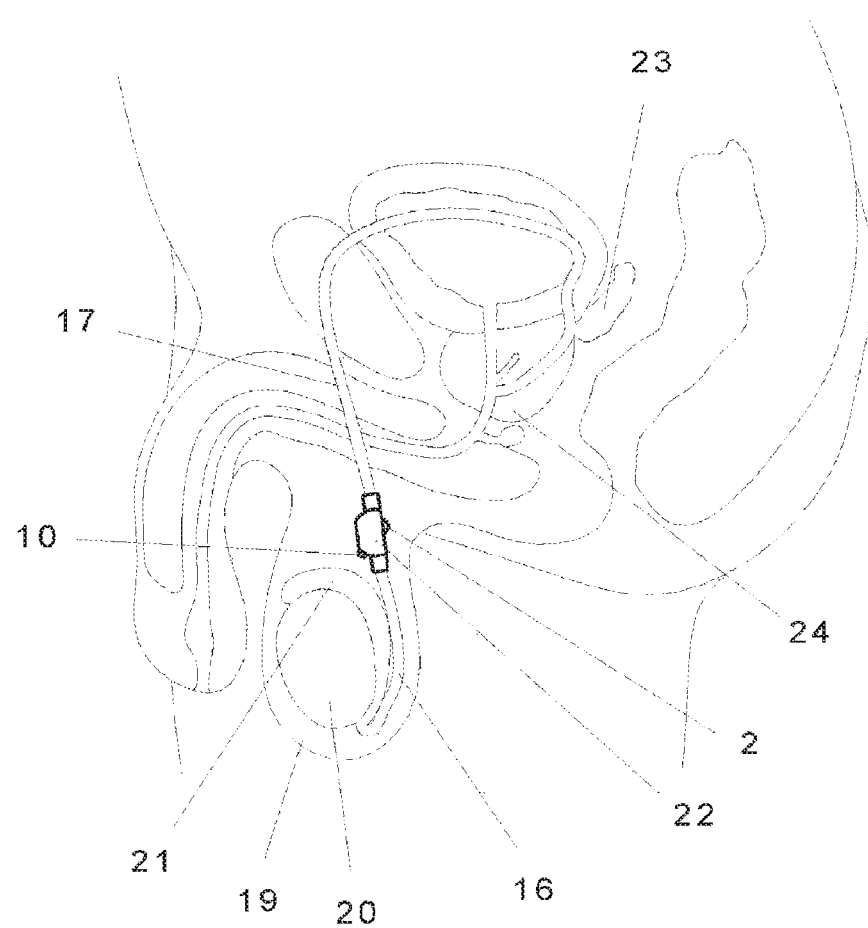
FIG. 1 shows a schematic cross-section through the genitals of a man, illustrating the position of the sperm duct valve according to an embodiment of the invention in the sperm duct in the region of the scrotum.
Figure 2:
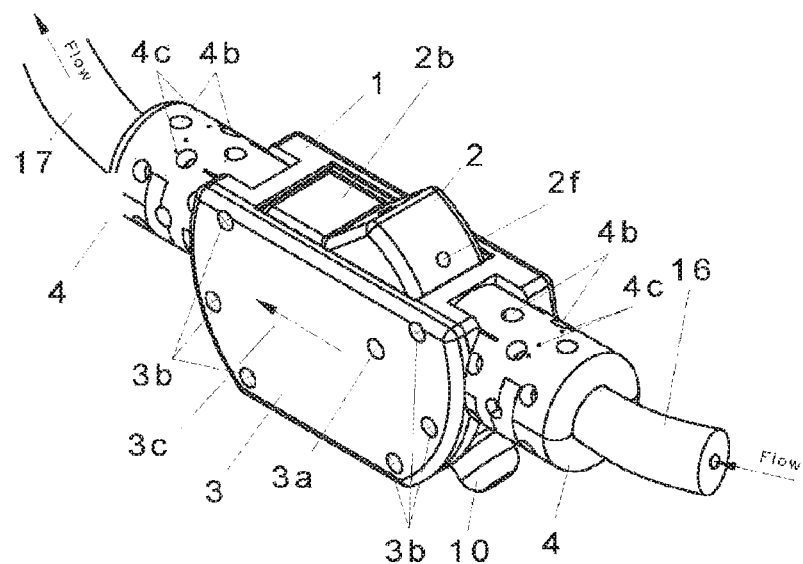
FIG. 2 shows the view of the sperm duct valve according to an embodiment the invention in the open position, said valve being connected to the ends of a severed sperm duct. The flow direction of the sperm through the sperm duct valve from the testicular sperm duct end to the abdominal sperm duct is denoted by arrows and "Flow".
Figure 3:
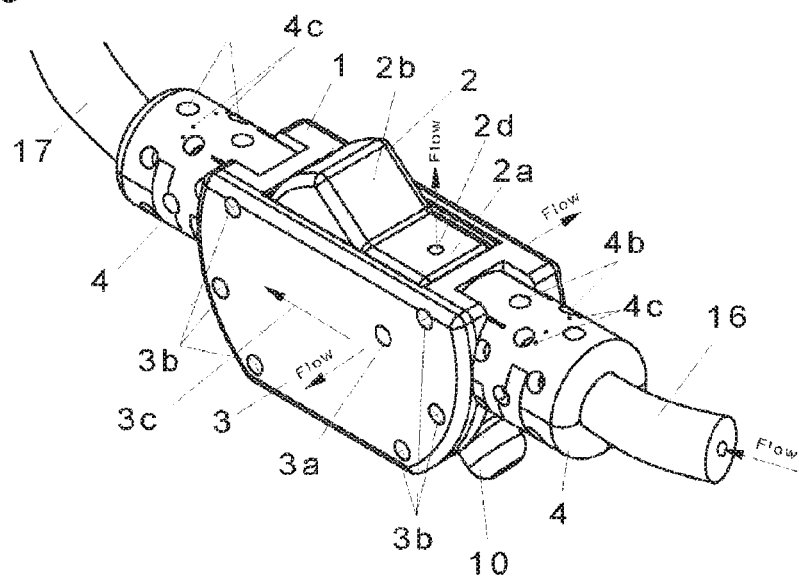
FIG. 3 shows the sperm duct valve connected to the sperm duct ends as in FIG. 2, but in the closed position. The flow direction of the sperm through the testicular sperm duct to the sperm duct valve is denoted by the arrows and "Flow". The sperm flow through the abdominal sperm duct is interrupted by the rocker switch in the closed position.
Figure 4:
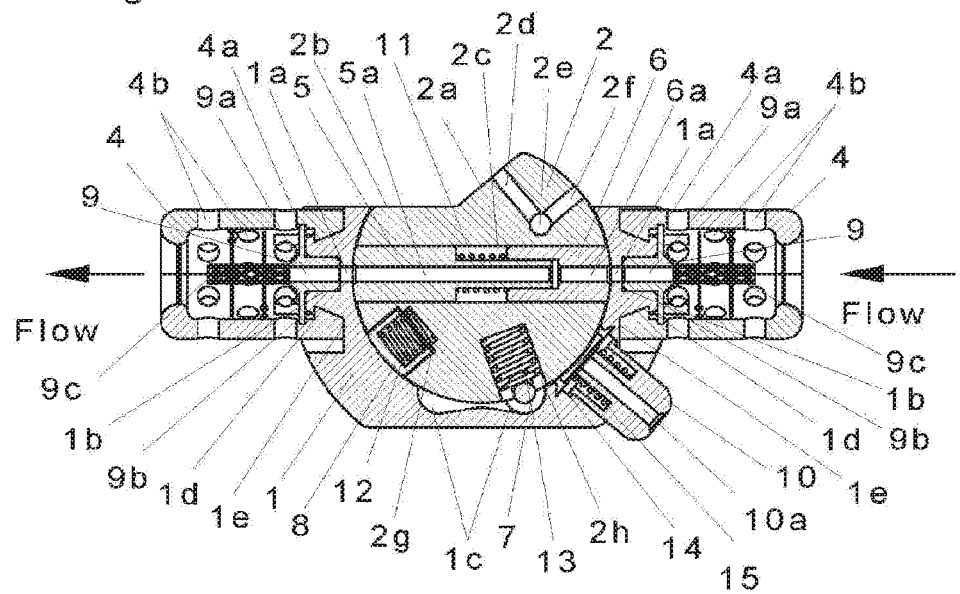
FIG. 4 shows a vertical longitudinal section through the sperm duct valve in the open state.
Figure 5:
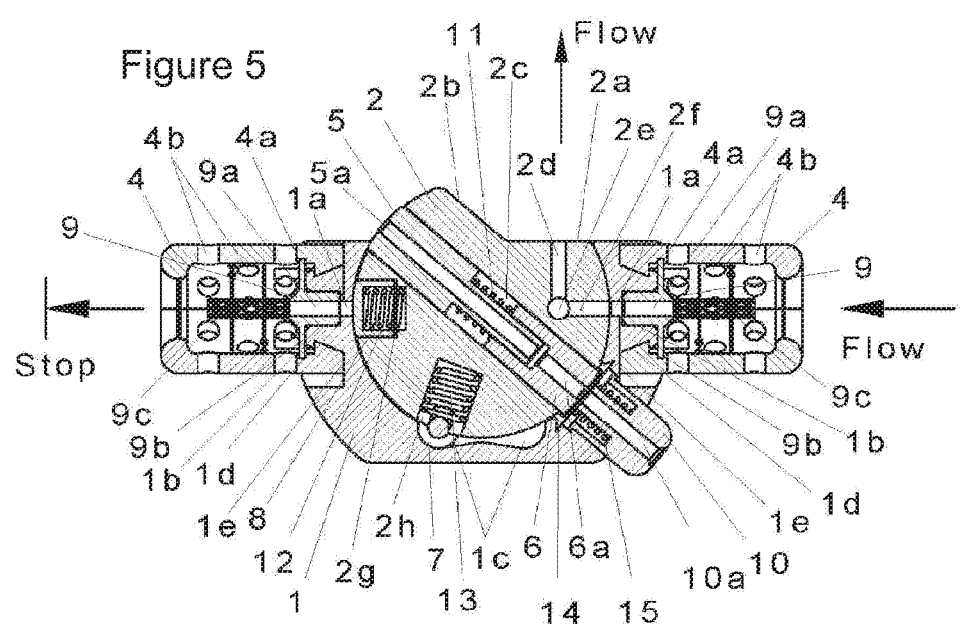
FIG. 5 shows a vertical longitudinal section through the sperm duct valve in the closed state.

The sperm duct valve 22 according to the example embodiment of the invention can be implanted in the sperm duct 16, 17 in the scrotum 19 of a man, as shown in FIG. 1. To this end, the sperm duct extending from the testis 20 is first severed, the end at the testicular part of the sperm duct 16 and the end at the abdominal part of the sperm duct 17 not being closed, as is the case for example in a vasectomy. In the diagram, the sperm duct valve 22 is implanted between the epididymis 21 and the vesicular gland (glandulae vesiculosa) 23, but still in the region of the scrotum 19. It need not necessarily be located close to the epididymis 21. The sperm duct valve 22 consists of a valve body 1 having side walls 3, valve connection pieces connected to the ends of the testicular and abdominal sperm ducts 16 and 17, as well as a rocker switch 2 and a release pin 10. Like the testes and the sperm ducts, the sperm duct valve is freely movable to a certain extent within the scrotum, according to any type of physical activity by the man. As shown in FIGS. 2-5, the illustrated embodiment of the invention consists of a valve body 1 which serves to accommodate valve connection pieces 9 with valve caps 4, said valve connection pieces being fitted laterally and opposite one another and being shown on the right and on the left in FIGS. 2 to 5, as well as the rocker switch 2 and the other mechanical parts. The valve body 1 has for example the shape of a cuboid with rounded, in some cases significantly rounded, corners and edges on all sides. The rounding prevents any trauma to the surrounding tissue. The valve body 1 has for example a length of around 18 mm, a height of 10 mm and a depth of around 7 mm. However, dimensions of up to 50% larger are also conceivable. The smaller the valve, the greater the wearing comfort. However, the user friendliness of the rocker switch 2 then decreases, and vice versa. The specified dimensions have been tried by self-experimentation and have been confirmed to be a good compromise.

Most parts are preferably made of implant plastic, such as for example PEEK, and are worked by micro-injection molding and/or CNC milling. The valve connections 9 may be made of metal alloys, such as for example titanium alloys (for example nitinol) or a suitable implant steel (for example the material 1.4441/316 LVM), or of plastic or of a combination of both types of material. However, the lattice-type small tube 9c may also be made for example of metal and may be incorporated by means of injection molding into the parts 9b and 9a made of plastic for example. The necessary compression springs may be made of implant spring steel or platinum alloys.

The valve body 1 has, in the top third in the longitudinal direction, a through-channel 1a having a diameter of around 0.7 mm, which extends through the rocker switch 2 and the valve connection pieces 9 and through which sperm can flow in the open state of the valve. Located at the end sides of the cuboid-shaped valve body, axial to the through-channel 1a, are wedge-shaped cutouts 1d and circular cutouts 1e for receiving the valve caps 4 and stepped bores 1b for receiving the valve connection pieces 9 during implantation. Located transversely to the through-channel 1a and extending from the large flat surface 3 of the valve body is a large stepped bore which is perpendicular to the through-channel 1a, said large stepped bore having for example a diameter of 12 mm and a depth of 5 mm. Located in the same axis and in the bottom of the large stepped bore is a smaller blind bore having for example a diameter of 2 mm and a depth of 0.7 mm. This small blind bore serves to receive and rotatably mount the rocker switch 2. The large stepped bore intersects the upper edge of the valve body, as a result of which the installed rocker switch 2 protrudes from the valve body. Located in the bore wall in the lower region of the stepped bore are two identical cutouts 1c which are mirror-symmetrical to one another and each have the shape of at least one segment of a circle. These serve as a guide and stop for a sprung wheel axle 7 which brings the rocker switch 2 into the two end positions. The wheel axle 7 provides for the switching of the rocker switch 2. It has the shape of a dumbbell. In the region of the axle, it is pressed by means of the axle spring 13, which is a normal compression spring, out of its guide in the rocker switch 2. The pair of wheels on the axle must thereby automatically follow the shape of the cutouts 1c in the valve body 1 and thus force the rocker switch 2 into the respective end stop for "open" or "closed". The valve can thus assume only a fully closed or fully open state.

Located in the left-hand bottom corner, at an angle of for example 40° to the through-channel 1a, there is a continuous stepped bore and a wedge-shaped cutout for accommodating a securing device consisting of the release pin 10, a release pin spring 15 and a securing plate 14.

Due to the bores and rounded areas, the cuboid-shaped valve body 1 has a sickle-shaped main surface. Located on this narrow edge are a plurality of, for example 6, cylindrical pins. The valve body 1 can thus be connected to the valve cover 3 for example by means of ultrasonic spot welding. The valve cover 3 thus closes off the entire valve technology with respect to the outside.

The rocker switch 2 has the shape of a cylinder of small height, the cylinder jacket of which faces towards the valve connections, with a cylinder bottom and cylinder top which are oriented parallel to the side walls 3 of the valve body. The cylinder jacket of the rocker switch 2 has a cutout with surfaces 2a and 2b, which extends over barely one-quarter of its circumference. The cutout in the rocker switch 2 thus consists of two surfaces 2a and 2b which are perpendicular to the cylinder bottom and cylinder top and form the angle of the cutout, for example 140°. In the open position of the valve 22, the surface 2b is flush with the valve body 1 while the surface 2a protrudes from the valve body. In the closed position, the surface 2a is flush with the body while the surface 2b protrudes. In addition, the surface 2a is located close to the testicular inlet end of the valve (in FIGS. 2-4, the inlet end of the valve is denoted by the arrow "Flow" pointing into the valve), said surface running flush with the valve body at the inlet end when the valve is closed. In a corresponding manner, the surface 2b is located close to the abdominal outlet end of the valve and runs flush with the valve body at the outlet end of the valve when the valve is open. (In FIGS. 2 and 4, the outlet end of the valve is denoted by the arrow "Flow" pointing out from the valve.)

The rocker switch 2 is rounded on all sides and has a plurality of bores. Among these, a first bore 2c leads parallel to the cylinder top and cylinder bottom and through the center of the cylinder 2 and parallel to the surface 2b. This bore enables sperm to flow when the valve 22 is open, and to this end accommodates sliding tubes having an outer seam 5 and a sliding tube having an inner seam 6, which are pressed outwards by a compression spring 11. As a result, a passage for the sperm which is sealed off from the outside is provided in the open state of the sperm duct valve 22 as a result of the spring and the suitably curved geometry of the outer end faces of the sliding tubes 5 and 6 and the bores 5a and 6a thereof together with the through-bores 1a in the valve body and the bore 9a in the valve connection piece 9. Further bores 2d and 2f likewise extend parallel to the cylinder top and lead from a first opening on the cylinder jacket in the region of the inlet end 4a of the valve, axial with the opposite stepped bore 2g of the valve, and from a second perpendicular bore in the surface 2a into the interior of the rocker switch 2, wherein the bores 2d and 2f meet at a point of intersection. A further bore 2e intersects this point of intersection at right angles to said bores 2d and 2f and is aligned with a bore on the side of the valve 22 which leads to the outside. In the closed state of the sperm duct valve 22, the bore 2e is also aligned with a bore 3a in the valve cover 3 and a bore in the wall of the valve body 1 located precisely opposite the latter. The aforementioned bores serve to convey sperm away to the outside and into the interior of the scrotum 19 when the valve is closed.

The two surfaces 2a and 2b form the touch surfaces for switching the valve 22. When the surface 2b for "open" is pressed, the rocker switch 2 rotates in the valve body 1 through a predefined angle, for example 40°, and securely latches at this position. Pressing on the other surface 2a for "closed" causes the rocker switch 2 to spring back through 40° in the other direction. The rocker switch 2 accommodates in a blind bore 2g a blocking pin 8 and a pin spring 12 as sealing elements. The bore axis of the stepped blind bore 2g for accommodating the blocking pin 8 and the pin spring 12 extends parallel to the surface 2a "closed" and crosses at right angles the longitudinal axis of the cylindrical rocker switch 2. The sliding tube arrangement with bores 5a and 6a is located in a position rotated through the same predefined angle, for example 40°, relative to the bore axis for the blocking pin 8 and thus parallel to the surface 2b "open".

Located in a further bore 2h, which is diametrically opposite the surface 2a and 2b, is the wheel axle spring 13 which pushes the wheel axle 7 out of the rocker switch 2 and ensures the latching effect. To this end, the wheel axle 7 is guided in precisely dimensioned guide grooves in the rocker switch 2 in the region around the bore 2h. Additionally arranged in the valve body on this side of the rocker switch 2 are two cutouts 1c, in which the sprung wheel axle 7 is received with little play and with a precise displacement travel. The cutouts, on the sides thereof facing towards the connection pieces, are shaped as a segment of a circle so that the wheel axle 7 is arrested there. The cutouts 1c, on the side thereof facing towards the middle of the valve, each have a surface angled upwards towards the rocker switch 2, said surfaces meeting in the center line of the valve 22.

In the closed position of the valve, the wheel axle 7 is held in the outlet-side cutout 1c (on the left-hand side in the figure), and when the valve 22 is switched the wheel axle is moved into the inlet-side cutout 1c and is held therein (on the right-hand side in the figure). The sliding tube with the outer seam 5 and the sliding tube with the inner seam 6, which are mounted in the rocker switch 2, are manufactured in such a way that they can be inserted into one another and pushed out of one another by means of the compression spring 11, which is a normal compression spring. This seals off the through-channel 5a and 6a from the through-channel 1a of the valve body 1. The outwardly protruding ends of the sliding tubes to this end additionally have a curved geometry which corresponds to the shape of the large stepped bore in the valve body 1. When the valve is open, the sliding tube arrangement extends in the same axis as the valve passage. When the valve is closed by rotating the rocker switch 2 through 40°, the opening of one sliding tube points outwards into free space. The other sliding tube latches into the bore of the securing plate 14 at the bottom right-hand side. When the valve is to be closed, the release pin must first be pressed from below counter to the resistance of a release pin spring 15. Only then can the valve at the same time be opened. Like the sliding tubes, the release pin 10 has a through-bore 10a and in the closed state of the valve allows the cavities to be filled with the body fluid of the sliding tubes. A securing plate 14 is an inwardly curved trapezoidal plate with a stepped bore and is pushed into the corresponding cutout in the valve body 1 during assembly of the valve following the insertion of the release pin 10 and the release pin spring 15. The release pin spring 15 may be configured as a multi-component plate spring or as a normal compression spring. With the plate spring variant, a click effect can be achieved which indicates that the release pin 10 has been released.

The actual stoppage of the sperm flow, by the closed valve, is ensured by the blocking pin 8. As the valve is closed, said blocking pin is pushed in front of the abdominal through-hole in the valve interior, that is to say the outlet opening of the valve in the region of the outlet end thereof. Correspondingly, the outlet end in FIG. 5 in the blocked scenario is denoted by an arrow "Stop", wherein the sperm nevertheless flow off through the run-off channel 2f, 2e and 2d. The blocking pin 8 is pressed against the large stepped bore wall of the valve body by means of the pin spring 12, which is a normal compression spring, and on the surface which makes contact with the valve body 1 has the same curved geometry. In this way, the sperm duct valve 22 does not require any elastic sealing materials which are subject to wear. It does not lose its sealing effect over a long period of use, as is usually the case with valves. By virtue of the low friction in the region of the path described by the blocking pin on the valve body 1, both sides actually grind into one another and accordingly an increasingly improved sealing effect is achieved. Then again, given the low switching frequency of probably less than 10 times over the lifelong period of use, the expected wear is negligible.

For a sperm having a head diameter of around 3.5 micrometers, there is no way through this barrier, especially since the sperm in the region of the sperm duct are still within an acid barrier, in other words are themselves unable to move.

A cylindrical journal (not shown) on each side of the rocker switch 2 serves as the rotation axle, precisely in the mid-point of the rocker switch 2, said cylindrical journals protruding from the surface of the cylinder top and cylinder bottom. The journals enter the blind bores (not shown) of the valve body on one side and the blind bore of the valve cover 3 on the other side.

The valve cover 3 is in principle a mirror image of the large side wall of the valve body. After assembly, it closes off the entire mechanism from the outside. To this end, it has a plurality of, for example 6, bores 3b for receiving corresponding pins on the valve body 1, in order to be able to be welded to the latter with a precise fit. Alternatively, however, the valve cover 3 could also be screwed to the valve body 1 or connected to the valve body 1 by latching.

As shown in FIGS. 6-9, the valve connection pieces 9 have a large flange 9b which, during implantation, is clamped by the two-part valve cap 4 in the grooves 4a of the latter. Located on the connection-side direction of the valve body 1 is a cylindrical connector which, during assembly of the unit consisting of sperm duct 16/17, valve connection 9 and the two-part valve cap 4, can be plugged into the bore 1b of the valve body 1 as shown in FIG. 9. Located on the opposite side is a thin-walled small tube 9c for holding the respective sperm duct end. The valve connection piece 9 has a continuous opening which leads through the connector, the flange and the small tube and ensures the flow of the sperm. In one embodiment of the invention (not shown), the small tube 9c has a plurality of fine conical graduations, as in the case of a hose fitting. During implantation, a plurality of finely graduated different internal diameters of the small tube are available for the purpose of adapting to the sperm duct. In a further embodiment of the invention, the small tube 9c is provided with a lattice-like structure in the outer surface. As in the case of a stent, the lattice structure is compressed somewhat prior to implantation. Moreover, this end is also sheathed with a thin silicone layer (not shown), for example a silicone hose or a similar elastic inert material, in order to ensure the sealing of the inner sperm duct mucosa to the valve connection piece 9 in the region from 9c to 9b. Once the valve connection pieces 9 have been inserted into the sperm ducts 16, 17, they are widened from inside onto the nominal inner mass. This takes place by pulling an elongate, needle-like element 18 with a wedge-shaped head out of the valve connection piece 9.

The valve connection piece 9 with a minimal external diameter can thus easily be inserted into the small lumen of the sperm duct. By means of special pliers (not shown), similar to the principle of blind riveting pliers, the element 18 is pulled out of the valve connection piece 9 and slightly widens the lumen of the valve connection in the region of the lattice structure together with the sperm duct 16, 17 itself.

Another variant of the widening of the lattice structure of the valve connection piece 9 is also possible using the reverse principle by pressing inwards a cylindrical mandrel having a conical tip, instead of the illustrated embodiment 18, with the aid of similar special pliers which are likewise not shown.

By virtue of their bulging rounded shape, the hollow-cylindrical valve caps 4 protect the sperm ducts 16, 17 against piercing by the valve connections in the event of extreme movements. The outer surfaces of the valve caps 4 are provided with bores all around, through which the sperm duct ends always remain in contact with the natural fluid of the surrounding tissue and enable substance exchange. A valve cap 4 consists of two halves which are provided with hooks 4d and cutouts. By virtue thereof, the two halves can be plugged together and at the same time the valve connection piece 9 can be fixed therein.

When plugged together, the two halves form a hollow cylinder. On the side facing towards the sperm duct 16, 17, it has a large rounded edge and an inwardly directed bead. The internal diameter of the bead should correspond to the external diameter of the sperm duct. Facing towards the valve, the valve caps 4 have in the interior a groove 4a for receiving a flange 9b of the valve connection 9. To this end, use is made of special pliers (not shown) which are provided with a holding device for the valve cap halves 4. The two halves can thus be pressed together in a secure, precise and forceful manner. The valve cap halves 4 latch into one another.

Microneedles 4e are also incorporated in the halves. Said microneedles are arranged in such a way that they pierce the muscular walls of the sperm duct tangentially when the valve cap halves are pressed together, and enter holes formed on the opposite valve cap half 4 without exiting from the other side thereof. This ensures a secure connection of the sperm duct valve to the sperm duct 16, 17 without restricting or jeopardizing the blood supply to the sperm duct through strangulation or any other suture. The large flange of the valve connection piece 9 embeds in the internal groove 4a of the valve cap halves 4.

Finally, the resulting unit consisting of connection piece 9, sperm duct 16, 17 and valve cap halves 4 is plugged into the sperm duct valve. By virtue of the hooks 4f, it likewise latches therein into the latching elements 1d and the circular groove-like cutout 1e of the valve body 1. The described steps in FIGS. 6 to 10 take place both with the abdominal sperm duct end 17 and with the testicular sperm duct end 16. A non-releasable connection of the sperm duct to the valve is thus obtained. This connection could also be constructed in such a way that it can be released again by means of a further special tool.

Inert materials are preferably used for the sperm duct valve according to embodiments of the invention. The surfaces of the individual parts thus require no anti-adhesion coatings and medicaments to avoid rejection reactions of the human body.

In one embodiment of the invention, a surface treatment which is limited to individual parts or is widened to all parts of the sperm duct valve 22 is optionally provided for the aforementioned purpose.

In order to be able to react to the different anatomical dimensions of the sperm ducts 16, 17 of different men, the valve connections 9 and valve caps 4 are accordingly manufactured in different sizes. The surgeon can thus choose the appropriate size during implantation. The valve body 1 itself, along with the internal parts, could always remain the same size. An implantation of the sperm duct valve according to aspects of the present invention is thus also suitable as an alternative to a vasovasectomy when the two sperm duct ends 16, 17 of a sperm duct have different dimensions, as is often the case after a vasectomy that took place years earlier.

Upon closing the sperm duct valve, the user is not sterile immediately but rather only after weeks to months. This need not be viewed as a disadvantage. Once pregnancy has been achieved for example in a partnership where there is a desire for children, the valve is closed. The user is then sterile at the latest at the time the child is born, that is to say around 9 months after conception. Further contraceptive measures by the woman or the man are no longer necessary. Only when there is a desire for a further child, for example after 2-4 years, will the sperm duct valves be opened. Things then happen more quickly. Sperm could be detected in the ejaculate for example after 4 weeks or already at the time of first ejaculation after implantation of the newly developed sperm duct valve, even though the man had previously been sterile for a year.

Apart from the condom, all male contraceptives, including medicaments and also the invention described herein, have the disadvantage that the user is not sterile immediately after activating the blocking function or taking the medicament. Sperm may still remain for weeks or months in the organs downstream of the respective device, such as the prostate gland 25 (Prostata) and the vesicular gland 26 (Glandulae vesiculosa), and may trigger undesired fertilization with an ejaculation during sexual intercourse.

It is therefore advisable to have the desired sterility scientifically confirmed beforehand by means of a spermiogram.

In addition, these methods do not protect against infectious diseases.

Aspects and features of the embodiments described above may be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled.

The invention claimed is:

1. An implantable sperm duct valve for contraception for use in a man or male animal, for regulating the sperm flow in the abdominal sperm duct or vas deferens within the scrotum, comprising a valve configured to be attached to the testicular end and the abdominal end of a severed sperm duct by valve connection pieces, and a manual switch for changing the state of the valve, the switching state of which can be ascertained externally by palpation and can be changed between an open state and a closed state wherein the sperm duct valve has a through-channel which in the open state of the sperm duct valve is configured to lead from a first one of the valve connection pieces at the testicular end of the sperm duct to a second one of the valve connection pieces at the abdominal end of the sperm duct and in the closed state of the sperm duct valve is configured to be blocked at the end of the through-channel facing towards the abdominal end of the sperm duct and has at least one run-off channel which in the closed state of the valve is configured to lead from the first one of the valve connection pieces at the testicular end of the sperm duct out of the sperm duct valve and into the body of the man or male animal.

2. The implantable sperm duct valve according to claim 1 wherein the valve connection pieces each comprise a small tube, the wall of which has conical graduations on the outside.

3. The implantable sperm duct valve according to claim 2 wherein valve connection pieces are accommodated in valve caps of the sperm duct valve.

4. The implantable sperm duct valve according to claim 3 wherein microneedles are arranged in the valve caps for attaching the valve caps to walls of the sperm ducts.

5. The implantable sperm duct valve according to claim 4 wherein the valve caps have openings which lead externally of the valve and ensure that the sperm ducts make contact with body fluid.

6. The implantable sperm duct valve according to claim 3 wherein the valve caps have internal grooves for receiving the valve connection pieces.

7. The implantable sperm duct valve according to claim 3 wherein the valve caps each consist of two halves which can be plugged together.

8. The implantable sperm duct valve according to claim 2 wherein the valve connection pieces of the sperm duct valve are made of metal alloys or plastic or of a combination of both types of material.

9. The implantable sperm duct valve according to claim 1 wherein a release pin with a release pin spring is arranged on the switch.

10. The implantable sperm duct valve according to claim 9 wherein the release pin has openings which lead out of the valve.

11. The implantable sperm duct valve according to claim 1 wherein the valve connection pieces each comprise a small tube, the wall of which is provided with a lattice structure.

12. The implantable sperm duct valve according to claim 11 wherein the lattice structure of the small tube is entirely or partially sheathed with silicone or an elastic inert material.

13. The implantable sperm duct valve according to claim 1 wherein the switch is configured as a rocker switch.

14. The implantable sperm duct valve according to claim 1 wherein the through-channel in a region of the switch is arranged in a sliding tube having an inner seam and an outer seam and a compression spring.

15. The implantable sperm duct valve according to claim 1 wherein the switch has a blocking pin with a spring for blocking the through-channel at the outlet end of the sperm duct valve.

16. The implantable sperm duct valve according to claim 1 wherein the switch has a wheel axle with a spring and cutouts for receiving the wheel axle in a latching manner.

17. The implantable sperm duct valve according to claim 1 wherein individual parts of the sperm duct valve or the entire sperm duct valve is/are coated with medicaments or anti-adhesion coatings.

* * * * *